US010971269B2

(12) United States Patent
Kartoun et al.

(10) Patent No.: US 10,971,269 B2
(45) Date of Patent: Apr. 6, 2021

(54) TREATMENT RECOMMENDATION DECISION SUPPORT USING COMMERCIAL TRANSACTIONS

(71) Applicant: International Business Machines Corporation, Armonk, NY (US)

(72) Inventors: Uri Kartoun, Cambridge, MA (US); Fang Lu, Billerica, MA (US); Kenney Ng, Arlington, MA (US); Yoonyoung Park, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 606 days.

(21) Appl. No.: 15/835,735

(22) Filed: Dec. 8, 2017

(65) Prior Publication Data
US 2019/0180870 A1    Jun. 13, 2019

(51) Int. Cl.
*G16H 50/20*    (2018.01)
*G16H 50/70*    (2018.01)
(Continued)

(52) U.S. Cl.
CPC ............. *G16H 50/20* (2018.01); *G16H 10/60* (2018.01); *G16H 20/00* (2018.01); *G16H 50/70* (2018.01)

(58) Field of Classification Search
CPC ........ G06Q 50/22; G06Q 50/24; G06Q 40/08; G06Q 30/0236; G06Q 30/0226; G06Q 30/0207; G06Q 30/0234; G06Q 30/0215; G06Q 30/0238; G16H 50/30; G16H 50/20; G16H 10/60; G16H 15/00; G16H 20/30;
(Continued)

(56) References Cited

U.S. PATENT DOCUMENTS 5,937,387 A *  8/1999  Summerell ......... G06F 19/3456
                                                    705/2
6,039,688 A *  3/2000  Douglas .............. G06F 19/3475
                                                    600/300
(Continued)

OTHER PUBLICATIONS

"The Era of Cognitive Systems: An Inside look at IBM Watson and how it works", IBM Corporation, IBM Software Group, Whitepaper, IBM Watson Solutions, Sep. 2012, 19 pages.
(Continued)

*Primary Examiner* — Joseph D Burgess
(74) *Attorney, Agent, or Firm* — Stephen J. Walder, Jr.; William J. Stock

(57) ABSTRACT

Mechanisms are provided to implement a cognitive medical decision support system that operates to analyze a set of commercial transactions executed by a patient to identify at least one of products or services purchased during each commercial transaction or an activity, associated with the commercial transaction, engaged in by the patient. The cognitive medical decision support system determines a lifestyle behavior pattern of the patient based on the products, services, or activities associated with the commercial transactions in the set of commercial transactions and evaluates an impact of the lifestyle behavior pattern to at least one of the overall health of the patient, a specific medical condition of the patient, or a specific previously prescribed treatment of the patient. The cognitive medical decision support system outputs a notification indicating the impact of the lifestyle behavior pattern.

20 Claims, 5 Drawing Sheets

(51) Int. Cl.
G16H 10/60 (2018.01)
G16H 20/00 (2018.01)

(58) Field of Classification Search
CPC ........ G16H 20/60; G16H 20/10; G16H 50/70;
G06N 20/00; G06N 20/20; G06F 19/00;
G06F 19/324
See application file for complete search history.

(56) References Cited

U.S. PATENT DOCUMENTS

| | | |
|---|---|---|
| 6,401,072 B1 | 6/2002 | Haudenschild et al. |
| 2009/0125335 A1 | 5/2009 | Manetta et al. |
| 2014/0180784 A1* | 6/2014 | Martin ............... G06Q 30/0215 |
| | | 705/14.17 |
| 2014/0310016 A1 | 10/2014 | Kenney et al. |
| 2015/0169839 A1* | 6/2015 | Zhang ................... G06Q 40/12 |
| | | 706/12 |
| 2016/0364547 A1 | 12/2016 | Love et al. |

OTHER PUBLICATIONS

Deleger, Louise et al., "Building Gold Standard Corpora for Medical Natural Language Processing Tasks", American Medical Informatics Association, AMIA Annual Symposium Proceedings, vol. 2012, Nov. 3, 2012, pp. 144-153.
Demner-Fushman, Dina et al., "What can Natural Language Processing do for Clinical Decision Support?", National Institutes of Health, Author Manuscript, J Biomed Inform., vol. 42, No. 5, Oct. 2009, pp. 760-772.
List of IBM Patents or Patent Applications Treated as RElated, Oct. 31, 2018, 2 pages.

* cited by examiner

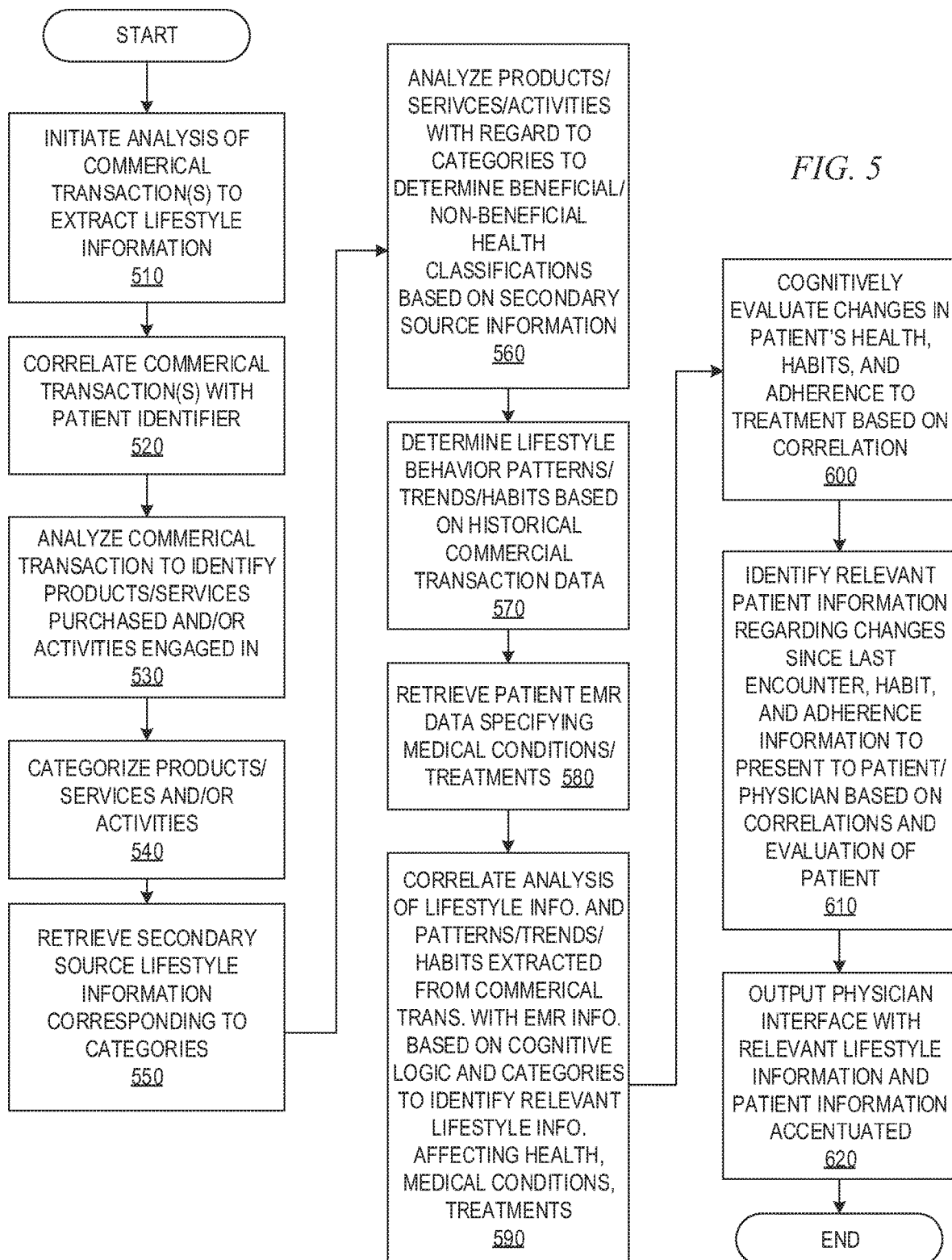

TREATMENT RECOMMENDATION DECISION SUPPORT USING COMMERCIAL TRANSACTIONS

BACKGROUND

The present application relates generally to an improved data processing apparatus and method and more specifically to mechanisms for providing treatment recommendation decision support using commercial transactions.

Decision-support systems exist in many different industries where human experts require assistance in retrieving and analyzing information. An example that will is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a cognitive medical decision support system. The method comprises analyzing, by the cognitive medical decision support system, a set of commercial transactions executed by a patient to identify at least one of products or services purchased during each commercial transaction or an activity, associated with the commercial transaction, engaged in by the patient. The method also comprises determining, by the cognitive medical decision support system, a lifestyle behavior pattern of the patient based on the products, services, or activities associated with the commercial transactions in the set of commercial transactions. Moreover, the method comprises evaluating, by the cognitive medical decision support system, an impact of the lifestyle behavior pattern to at least one of the overall health of the patient, a specific medical condition of the patient, or a specific previously prescribed treatment of the patient. In addition, the method comprises outputting, by the cognitive medical decision support system, a notification indicating the impact of the lifestyle behavior pattern. In this way, the patient's commercial transactions may be utilized as a way to discern lifestyle behavior patterns of the patient automatically which may then be used to interact with the patient regarding the impact of their lifestyle behavior patterns on their health, specific medical conditions, and/or treatments.

In some illustrative embodiments, the method further comprises determining, by the cognitive medical decision support system, at least one recommendation for treating the patient based on the determined impact of the lifestyle behavior pattern. The at least one recommendation may comprise at least one of a recommended modification to a previously prescribed treatment or a recommendation of a new treatment to be prescribed to the patient. In this way, the patient's lifestyle behavior patterns may be used as a way to suggest to medical personnel a treatment or modification of a treatment to consider when treating the patient.

In some illustrative embodiments, determining the impact of the lifestyle behavior pattern further comprises analyzing, by the cognitive medical decision support system, electronic medical records (EMRs) of a patient to identify a current treatment being performed to treat a medical condition associated with the patient; categorizing, by the cognitive medical decision support system, each product, service, or activity, associated with commercial transactions in the set of commercial transactions, into one or more of a set of predefined categories; and determining, by the cognitive medical decision support system, whether one or more of the products, services, or activities has been categorized into one or more predefined categories that conflict with the current treatment being performed to treat the medical condition of the patient. In still further illustrative embodiments, determining the impact of the lifestyle behavior pattern comprises, responsive to one or more of the products, services, or activities being categorized into one or more of the predefined categories that conflicts with the current treatment being performed to treat the medical condition of the patient, outputting the notification comprises outputting, by the cognitive medical decision support system, a notification indicating that a product, service, or activity categorized into the one or more predefined categories that conflicts with the current treatment being performed to treat the medical condition of the patient impacts the current treatment. Moreover, in some illustrative embodiments, the warning or the notification is output to medical personnel responsible for the current treatment being performed by the patient. Thus, via the mechanisms of the illustrative embodiments, medical personnel may be notified when their patients are engaged in lifestyle behaviors that are contrary to the treatments prescribed or negatively affect the health or medical conditions of the patient.

In some illustrative embodiments, determining a lifestyle behavior pattern of the patient based on the products, services, or activities associated with the commercial transactions in the set of commercial transactions further comprises: retrieving secondary source lifestyle information, from at least one secondary source lifestyle information source computing system, corresponding to the products, services, or activities associated with the commercial transactions, wherein the secondary source lifestyle information provides detailed health information about the particular products, services, or activities; categorizing the products, services, or activities according to categorizations of the products, services or activities as being beneficial or non-beneficial to the health of the patient; and determining the lifestyle behavior pattern based on the categorization of the products, services, or activities.

In some illustrative embodiments, the set of commercial transactions are executed using one or more purchasing means that are registered by the patient with the cognitive medical decision support system Moreover, in some illustrative embodiments, the purchasing means comprises at least one of a credit card account identifier, a debit card identifier, an account identifier of an account associated with a provider of products, services, or activities, or a loyalty program identifier associated with a loyalty program of a provider of products, services, or activities.

In some illustrative embodiments, information for the set of commercial transactions is obtained from at least one of a computing system associated with a financial institution with which the patient has a relationship or one or more computing systems associated with commercial establishments with which the commercial transaction is associated. Furthermore, in some illustrative embodiments, evaluating, by the cognitive medical decision support system, the impact of the lifestyle behavior pattern further comprises: correlating, by the cognitive medical decision support system, the lifestyle behavior pattern with portions of an electronic medical record (EMR) for the patient based on categories of lifestyle behavior pattern information and categories of EMR information; cognitively evaluating, by the cognitive medical decision support system, the correlations of categories of lifestyle behavior pattern information and categories of EMR information to identify changes in patient health, habits, or adherence to a prescribed treatment; and identifying, by the cognitive medical decision support system, relevant patient information regarding changes since a last encounter between medical personnel and the patient based on the correlations, wherein the notification comprises an indication of the relevant patient information.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment. For example, in some illustrative embodiments, a computer program product comprising a computer readable storage medium having a computer readable program stored therein is provided, where the computer readable program, when executed on a computing device, causes the computing device to implement a cognitive medical decision support system which operates to analyze a set of commercial transactions executed by a patient to identify at least one of products or services purchased during each commercial transaction or an activity, associated with the commercial transaction, engaged in by the patient, determine a lifestyle behavior pattern of the patient based on the products, services, or activities associated with the commercial transactions in the set of commercial transactions, evaluate an impact of the lifestyle behavior pattern to at least one of the overall health of the patient, a specific medical condition of the patient, or a specific previously prescribed treatment of the patient; and output a notification indicating the impact of the lifestyle behavior pattern.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment. For example, in some illustrative embodiments, the instructions, when executed by the processor, cause the processor to implement a cognitive medical decision support system that operates to analyze a set of commercial transactions executed by a patient to identify at least one of products or services purchased during each commercial transaction or an activity, associated with the commercial transaction, engaged in by the patient, determine a lifestyle behavior pattern of the patient based on the products, services, or activities associated with the commercial transactions in the set of commercial transactions, evaluate an impact of the lifestyle behavior pattern to at least one of the overall health of the patient, a specific medical condition of the patient, or a specific previously prescribed treatment of the patient, and output a notification indicating the impact of the lifestyle behavior pattern.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 5 is a flowchart outlining an example operation of a commercial transaction analysis system in accordance with one illustrative embodiment.

DETAILED DESCRIPTION

Figure 1:
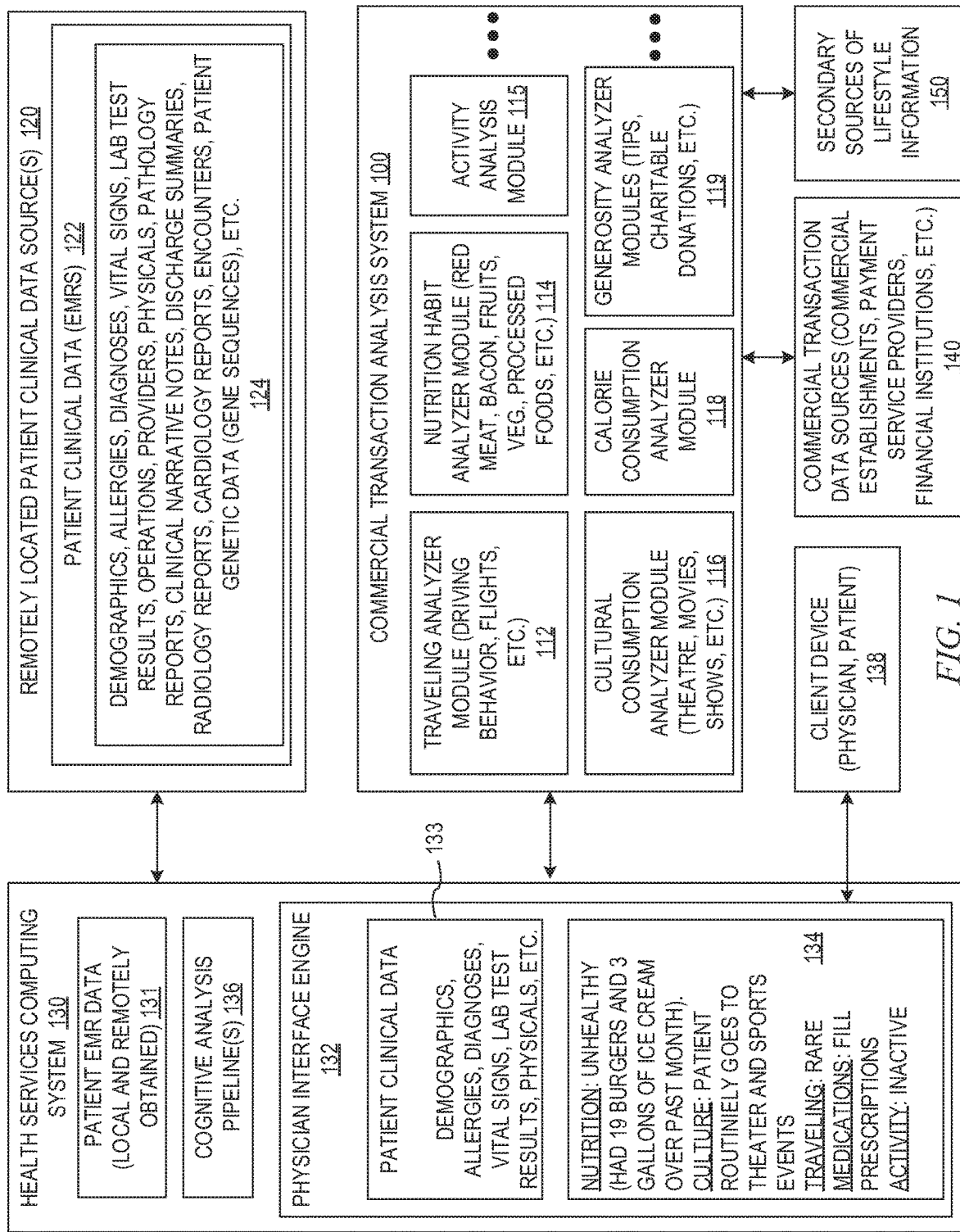
FIG. 1 is an example block diagram of a commercial transaction analysis system in accordance with one illustrative embodiment.

The strengths of current cognitive systems, such as current medical diagnosis, patient health management, patient treatment recommendation systems, cognitive medical decision support systems, law enforcement investigation systems, and other decision support systems, are that they can provide insights that improve the decision making performed by human beings. For example, in the medical context, such cognitive systems may improve medical practitioners' diagnostic hypotheses, can help medical practitioners avoid missing important diagnoses, and can assist medical practitioners with determining appropriate treatments for specific diseases. However, current systems still suffer from significant drawbacks which should be addressed in order to make such systems more accurate and usable for a variety of applications as well as more representative of the way in which human beings make decisions, such as diagnosing and treating patients. In particular, one drawback of current systems is that such systems do not adequately take into consideration lifestyle choices, habits, and activities of patients when determining diagnoses or treatment recommendations for patients and instead are directed to evaluating the patient's clinical data. It has been determined that a patient's lifestyle decisions, habits, and activities may have a great impact on the patient's overall health.

The illustrative embodiments provide mechanisms for automatically obtaining and utilizing a patient's lifestyle decisions, habits, and activities as a factor in providing medical decision support operations, which may include determining treatment recommendations for the patient's medical condition(s) or recommendations for modifying treatments for the patient's medical condition(s). In some illustrative embodiments, the mechanisms may include a cognitive medical decision support system, which in some embodiments may be a cognitive treatment recommendation system, that analyzes electronic medical records (EMRs) of a patient to identify a current treatment being performed to treat a medical condition associated with the patient. The cognitive medical decision support system may analyze a set of commercial transactions executed by the patient to identify at least one of products or services purchased during each commercial transaction and categorize each product or service into one or more of a set of predefined categories. Moreover, the cognitive treatment recommendation system may determine whether one or more of the products or services has been categorized into one or more predefined categories that conflict with the current treatment being performed to treat the medical condition of the patient. In addition, responsive to the one or more of the products or services being categorized into one or more of the predefined categories that conflicts with the current treatment being performed to treat the medical condition of the patient, the cognitive medical decision support system may output a warning or a notification indicating that a product or service categorized into the one or more predefined categories that conflicts with the current treatment being performed to treat the medical condition of the patient impacts the current treatment. Thus, the mechanisms of the illustrative embodiments may be integrated in, or operate with, a decision support system, which may be implemented as a cognitive system, which provides notifications and/or the recommendations based on lifestyle decisions, habits, and activities to appropriate medical personnel to assist them in making decisions regarding the treatment of the patient so as to improve the likelihood of a desired result in the patient's medical condition(s).

In particular, the illustrative embodiments recognize that information about the patient's lifestyle choices, habits, and activities (collectively referred to herein as "lifestyle information") may be obtained automatically from information gathered regarding commercial transactions that the patient engages in. That is, a patient's purchasing habits may provide insights into their lifestyle choices, habits, and activities, and ultimately provide reasons for their medical conditions which may be used to assist a physician or other medical personnel in treating the patient. For example, the foods that the patient eats, the medications the patient takes, the activities that the user engages in, their engaging in cultural activities, traveling, altruistic or generous activities, and the like, may be identified from correlation with commercial transaction information and used to identify additional factors for evaluating the patient's overall general health as well as health with regard to specific medical conditions and identify appropriate treatments.

In some illustrative embodiments, a commercial transaction analysis system is provided that monitors and analyzes a patient's commercial transactions at different commercial establishments, which may be preregistered with the system, to identify purchased items or services that may be indicative of lifestyle choices, habits, and activities that may impact the patient's medical condition and/or treatments that the patient is currently undergoing, e.g., products, services, or activities that may conflict with current treatments being performed to treat medical conditions of the patient or may introduce additional difficulties in the patient achieving particular goals of current treatments, e.g., weight loss, control of blood glucose levels, etc. The identification of commercial transactions corresponding to a particular patient may be based on the registration of user identifiers associated with commercial establishments (e.g., frequent buyer card information, club membership identifications, phone number of user, account identifiers, or the like) or payment service providers (e.g., credit card identifiers associated with credit card companies, bank card identifiers associated with banks or bank card issuers, etc.), or the like. In some illustrative embodiments, such commercial transaction information may be obtained from financial institutions with which the patient has a business relationship, e.g., the patient's credit card company, bank, or the like, where transactions are recorded and may be accessed to obtain statements and other financial records.

The illustrative embodiments may correlate purchase (commercial) information for a patient with other sources of information, e.g., nutritional information, medication information, activity information, information about particular products/services, and the like, that may then be used to identify factors that are relevant to the patient's medical condition and/or treatments. This information may then be presented to the medical professional when treating the patient, used by a computing system to automatically interact with the patient and/or medical professional, used by a cognitive system to generate treatment recommendations or recommendations for modifications in the patients' current treatment(s), etc. It should be noted that the medical condition may be a physical condition or a mental condition in this context.

The illustrative embodiments use commercial transactions, and potentially other sources of information that correlate with the products, services, and/or activities present in the commercial transactions, as a data resource that may be integrated with patient electronic medical record (EMR) data, and potentially other data feeds, so as to provide a cognitive medical system with information that informs the system what the patient tends to buy (e.g., cigarettes/vodka/bacon vs. milk/vegetables/vitamins) and how it relates to the patient's medical conditions, overall health, and/or particular treatments which the patient is currently undergoing. Further, in addition to the financial transactions themselves, also analyzing the specific bill may be performed, e.g., a credit card transaction of $20 may be stratified further to illuminate what specific dishes/ingredients were ordered during a meal, nutritional information may be correlated with the ordered meal, and that nutritional information may in turn be correlated with nutritional guidelines, the patient's weight information, the patient's current medical condition information (e.g., type 2 diabetes), and the patient's current treatments. It should be appreciated that in some embodiments, rather than having to obtain this information from credit card companies, bank card companies, or the like, some existing store loyalty programs, clubs, and the like, may be used as a source of this information.

In analyzing the commercial transaction information, the information may be analyzed to identify the particular products/services that were purchased, as well as the particular activities that the patient engaged in, and categorize those products/services/activities into a variety of different predefined categories, e.g., food, medication, entertainment, cosmetic services, physical training/gym services, health/medical services, etc. Based on the particular categorization, corresponding sources of secondary knowledge may be obtained for the categories and the product/service identities may be correlated with the secondary knowledge for that category, e.g., for food category, nutritional information may be retrieved from a centralized database, a computer system associated with the vendor of the food item, or the like. For a travel category, secondary information may be retrieved that provides information about the particular geographical regions traveled to, including known diseases to which travelers are exposed in those regions, nutritional information about how foods are prepared, etc. For an entertainment or cultural category, secondary information may be obtained that provides details of the type of entertainment involved, e.g., opera, musical theatre, action movie, types of musical performances, e.g., hard rock, classical, etc. Many other types of secondary sources of information may be accessed to obtain characteristics of the particular products/services/activities that the commercial transactions indicate the patient has purchased or engaged in.

In addition, from the commercial transaction information, e.g., credit card number, bank card number, commercial establishment's loyalty program identifier, phone number entered, etc., an identity of the patient may be obtained and corresponding EMR data may be retrieved for the patient. The patient's current medical conditions, treatments, etc., may be retrieved from the EMR data and corresponding relevant information that is relevant to the medical conditions, treatment, or overall health of the patient may be extracted from the collected commercial transaction and secondary information. Correlations of patient EMR data with the relevant health information extracted from the commercial transactions may be based on the predefined categories noted above with cognitive logic being employed to identify what categories of extracted health information have an impact on particular categories of patient EMR data, medical conditions, treatments, etc. The relevant information may then be analyzed by the cognitive logic, in accordance with guideline information for the medical condition, treatments, or overall health of the patient, to identify the impact of the patient's lifestyle choices on the patient's medical condition, treatments, and overall health. This relevant information may be analyzed along with other compiled relevant information over a predetermined period of time to identify behavior patterns, trends, habits, or the like, with these behavior patterns/trends/habits being evaluated by the cognitive system relative to the guidelines as well to thereby identify the impact of the patient's lifestyle choices over a period of time to their medical condition, treatments, and overall health.

Based on the results of the analysis, warnings, notifications, and the like may be output to the physician so that the physician can communicate with the patient or otherwise provide awareness to the physician when interacting with the patient as part of the physician's treatment of the patient. In addition, the commercial transaction data can be analyzed to see whether there are any special areas of concern, such as instances of transactions that occurred in different geographic regions which may cause urgent concerns (e.g., ingesting foods in a geographical region known to have parasites present in the food supply, traveling to a geographical region where there is a known disease outbreak, etc.) or otherwise may have an impact on the patient's health.

For example, if a patient travels to a place where there is a high level of risk for a disease or infection, this information can be retrieved to provide relevant background for better understanding the patient's health. Such information may be used to both identify negative factors, e.g., higher level of risk of a disease or infection, as well as positive factors, such as traveling in different regions where the food is made in a relatively healthy fashion. For example, even though the name of the food or dish is still the same between regions, in one particular region the food or dish may be known to be prepared with relatively less oil, sodium and sugar being added, indicating a lower negative health impact or even a greater beneficial impact on the patient's health.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for extracting patient health information from commercial transactions to generate treatment information. The illustrative embodiments of the present invention utilize automated specially configured computing systems that automatically extract information from commercial transactions which may be correlated with patient electronic medical record (EMR) information as well as secondary sources of knowledge to discern lifestyle information for the patient that may be relevant to the patient's medical condition(s), whether this be overall health of the patient or specific medical conditions the patient has previously reported, been diagnosed as having, or otherwise is receiving treatment for from a medical professional. The lifestyle information may then be cognitively analyzed in combination with other patient information extracted from the patient's EMR, to identify areas of concern to be brought to the attention of a medical professional treating the patient, to identify a diagnosis and/or recommended treatment for the patient to treat an identified medical condition, or to modify a previously prescribed treatment of the patient. In some cases, the results of the cognitive analysis may initiate automated communication with the medical professional, or with the patient themselves, to provide notifications of results of the cognitive analysis, which may include recommended treatments, modifications of treatments, or even notifications of an identified trend or pattern in lifestyle information of the patient.

FIG. 1 is an example block diagram of a commercial transaction analysis system in accordance with one illustrative embodiment. As shown in FIG. 1, the commercial transaction analysis system 100 may communicate with a health services computing system 130, one or more commercial transaction data sources 140, and secondary sources of lifestyle information 150. The commercial transaction analysis system 100 may comprise health services computer system 130 interface logic, a network interface for communicating with the commercial transaction data sources 140 and secondary sources 150, as well as other control logic for orchestrating the operations of the commercial transaction system 100 and the various analysis modules 112-119 of the commercial transaction analysis system 100. This logic is not explicitly separately shown in FIG. 1, but is considered to be present in the commercial transaction analysis system 100 as well as other logic for performing functions or operations not specifically attributed to the individual analyzer modules 112-119.

The health services computing system 130 may be any computing system associated with a provider of health services, such as a hospital, physician's office, pharmacy, clinic, laboratory, medical imaging facility, or the like. The healthcare services computing system 130 stores or has access to patient EMR data 131 that is specific to the healthcare services computing system 130 stored locally, and/or remotely located patient EMR and clinical data, such as may be accessed via a network interface and one or more data networks from a remotely located computing system, such as remotely located patient clinical data source(s) 120. The health services computing system 130 may be itself a computer that a physician accesses to obtain information about the patient, or may be a server or other computing device that provides data to client computing devices 135, such as portable tablet computing devices, workstations, or the like, that the physician may use to access the patient information. For example, the healthcare services computing system 130 may be a server located in a healthcare facility, such as a hospital, physician's office, clinic, or the like, and the physician or other healthcare worker may utilize a client computer 135 in an exam room, a portable tablet computing device 135, or the like, that has a communication connection with the healthcare services computing system 130 to access patient information from the server for display on the client computer, e.g., the physician interface 132 which will be described hereafter. Moreover, in some cases the client device 135 may in fact be a client device associated with the patient through which the patient may access the physician interface engine 132 to obtain information about their own health, medical conditions, and treatments. Appropriate privacy protections, as are generally known in the art, may be employed to ensure that unauthorized access to personal patient information is not permitted.

In some illustrative embodiments, the health services computing system 130 may interface with a commercial transaction analysis system 100 from which results of various analysis of lifestyle information extracted from commercial transactions, e.g., product/service purchases, activities engaged in, and the like, is performed to obtain lifestyle behavior pattern, habits, or trend information. The commercial transaction analysis system 100 obtains commercial transaction data from the commercial transaction data sources 140 and processes the commercial transaction data via one or more analyzer modules 112-119 to identify lifestyle behavior patterns, habits, or trends (collectively referred to herein as lifestyle pattern information) with regard to different categories of lifestyle pattern information.

Thus, the commercial transaction analysis system 100 monitors and analyzes a patient's commercial transactions at different commercial establishments, represented by commercial transaction data sources 140 which may be computing systems associated with the individual commercial establishments (e.g., individual stores, individual service providers, store chains, service provider chains, etc.), financial institutions with which the patient has a relationship (e.g., banks), payment service providers with which the patient has a relationship (e.g., credit card companies, online payment providers (such as Paypal™ or the like), etc. These commercial transaction data sources 140 may be preregistered with the commercial transaction analysis system 100, and may transmit commercial transaction data, via one or more data networks, to the commercial transaction analysis system 100 that identifies purchased items or services that may be indicative of lifestyle choices, habits, and activities that may impact the patient's medical condition and/or treatments that the patient is currently undergoing. For example, the commercial transaction data may specify the commercial establishment, the products/services/activities purchased, date/time data, quantity data, geographical location data where the commercial transaction took place (e.g., address, store number, phone number, indicator of online purchase, etc.), price paid, tip included, whether the commercial transaction was a charitable donation or performed with a charity organization, etc. The commercial transaction data may be pushed to the commercial transaction analysis system 100 from the commercial transaction data sources 140 on a periodic basis, at a scheduled time, or in response to an event, e.g., close-out of a day's transactions. Alternatively, the commercial transaction analysis system 100 may pull the commercial transaction data from the various preregistered commercial transaction data sources 140 on a periodic basis, at a schedule time, or in response to an event, e.g., initiation by a user, such as a physician requesting, via the health services computing system 130, to look at the patient's EMR data.

It should be appreciated that the commercial transaction data sources 140 may provide commercial transaction data for a plurality of different patients. The identification of commercial transactions corresponding to a particular patient may be based on the registration of user identifiers associated with commercial establishments (e.g., frequent buyer card information, club membership identifications, phone number of user, or the like) or payment service providers (e.g., credit card numbers associated with credit card companies, bank card numbers associated with banks or bank card issuers, etc.), with the commercial transaction analysis system 100. In some illustrative embodiments, such commercial transaction information may be obtained from financial institutions with which the patient has a business relationship, e.g., the patient's credit card company, bank, or the like, where transactions are recorded and may be accessed to obtain statements and other financial records. For example, the patient may pre-register with the commercial transaction analysis system 100, their various identifiers in a patient profile (not shown) which stores information about the patient's credit card or debit card numbers, loyalty program memberships, phone number, etc. Alternatively, the commercial transaction data sources 140 may have their own associations of such patient identifiers with the particular credit/debit card numbers, loyalty program memberships, phone numbers, etc. that the patient uses with those commercial transaction data sources 140 and may correlate such identifiers with a name or other general identifier of the patient that can be provided with details of the commercial transaction without divulging the individual credit/debit card numbers, loyalty program membership identifiers, phone number, etc. Any mechanism for correlating commercial transactions with individual identifiers of patients may be used without departing from the spirit and scope of the present invention.

The commercial transaction data obtained from the commercial transaction data sources 140 may be categorized by logic of the commercial transaction analysis system 100 into predefined categories of types of products/services/activities. That is, in analyzing the commercial transaction data received from the commercial transaction data sources 140, the commercial transaction data may be analyzed by the commercial transaction analysis system 100 to identify the particular products/services that were purchased, as well as the particular activities that the patient engaged in, and categorize those products/services/activities into a variety of different predefined categories, e.g., food, medication, entertainment, cosmetic services, physical training/gym services, health/medical services, cultural activities, travel activities, etc. In some cases, the same product/service/activity may be categorized into a plurality of categories depending on the particular implementation, e.g., a dinner theater purchase may be categorized into food, entertainment, and cultural.

The commercial transaction data, based on the categorization, may be provided to one or more corresponding analyzer modules 112-119 for further analysis and lifestyle pattern determinations. The particular analyzer modules 112-119 may also obtain information from secondary sources of lifestyle information 150 to assist in evaluating the commercial transaction data to generate an indication of lifestyle patterns for patients. That is, based on the particular categorization, corresponding sources of secondary knowledge may be obtained for the categories and the product/service/activity identities may be correlated with the secondary knowledge for that category, e.g., for food category, nutritional information may be retrieved from a centralized database, a computer system associated with the vendor of the food item, or the like. For a travel category, secondary information may be retrieved that provides information about the particular geographical regions traveled to, including known diseases to which travelers are exposed in those regions, nutritional information about how foods are prepared, etc. For an entertainment or cultural category, secondary information may be obtained that provides details of the type of entertainment involved, e.g., opera, musical theatre, action movie, types of musical performances, e.g., hard rock, classical, etc. Many other types of secondary sources of information may be accessed to obtain characteristics of the particular products/services/activities that the commercial transactions indicate the patient has purchased or engaged in.

Thus, for example, if a commercial transaction includes the purchase of a food item, e.g., from a restaurant, the overall commercial transaction information may be used to categorize the purchased item into a food category. As a result, secondary source lifestyle information from sources providing nutrition information may be accessed. The commercial transaction may be drilled own into to find the specific items purchased, e.g., the particular food item purchased, which can be used to match the food item with corresponding nutritional information from the secondary source lifestyle information. The correlation of commercial transaction data with secondary source lifestyle information may involve additional factors as well, such as the particular commercial establishment from which the food item was purchased, e.g., a "cheeseburger" from restaurant A may have different nutritional content than that of a "cheeseburger" from restaurant B. The nutritional information for the food item purchased may then be analyzed by the corresponding analyzer modules, e.g., nutrition habit analyzer module 114 and/or calorie consumption analyzer module 118, to determine a lifestyle behavior of the patient based on their nutritional information corresponding to commercial transactions the patient engages in. Similar correlations of secondary source lifestyle information specifying characteristics of a product/service/activity with the commercial transaction data may be performed for various other types of products/services/activities.

Thus, the analyzer modules 112-119, as one operation correlate the secondary source lifestyle information with the particular products/services/activities specified in the commercial transaction data received from the commercial transaction data sources 140. As further operations, the analyzer modules 112-119 may cognitively analyze and evaluate the correlated information to determined lifestyle behavior patterns, habits, and trends for a particular patient so as to provide insight information, i.e. lifestyle behavior patterns, to the health services computing system 130 that may assist the health services computing system in generating a physician interface via the physician interface engine 132 and/or perform other cognitive operations using cognitive analysis pipeline(s) 136. The analyzer modules 112-119 may apply cognitive analysis to the correlated information based on machine learned and trained logic for identifying patterns or trends in the correlated information leading to an assessment of lifestyle behaviors, patterns, and habits of the patient. For example, through a machine learning process, the nutrition habit analyzer module may learn that patients that eat foods that are high in a particular nutrient tend to be unhealthy, whereas if they eat other foods that are higher in a different nutrient, they tend to be more health, and may learn a particular weighting and balancing of these factors relative to one another in evaluating the healthiness of patient's nutritional habits.

The patterns, trends, and habits may be evaluated based on a single commercial transaction or a plurality of commercial transactions occurring over a predetermined period of time. Patterns, trends, and habits may be less accurately determined for smaller numbers of transactions, but may still have sufficient accuracy as to perform operations in the health services computing system 130 for presenting information to a physician via the physician interface engine 132 and/or performing other cognitive operations. For example, in one illustrative embodiment, the commercial transaction analysis system 100 may receive monthly statements from a credit card company for patients that have elected to utilize the services of the commercial transaction analysis system 100 and have given authorization for the credit card company to provide the monthly statement to the commercial transaction analysis system 100. The monthly statement may be evaluated with each commercial transaction occurring over the last month being categorized, correlated with secondary source lifestyle information, and analyzed and evaluated to determined patterns, behaviors, and habits regarding the way in which the patient conducts their life, i.e. what lifestyle choices the patient tends to make, the habits indicated by their purchases, and the like. For example, it may be determined that the patient is purchasing cigarettes once a week, indicating that the patient is not quitting smoking even though they may have informed their physician that they were quitting. As another example, the patient may be on a strict diet plan, however, their commercial transactions indicate that the patient visits a fast food restaurant at least twice a week. Various behaviors, habits, or trends in patient lifestyle may be extracted from analysis of the patient's commercial transactions.

It should be appreciated that, in some illustrative embodiments, the commercial transaction analysis system 100 may maintain patient profile data structures (not shown) for each of the patients that have registered for utilization of the commercial transaction analysis system 100. These patient profile data structures may store historical data regarding the results of the analyzer modules 112-119 generated for the patient over a predetermined period of time. This historical data may be evaluated by the analyzer modules 112-119 in combination with new commercial transaction data and secondary source lifestyle information obtained for a current time period so as to be able to perform such behavior, habit, or trend identifications for the patient. Thus, for example, in a previous month, the patient's nutritional behavior was to eat at fast food restaurants for every other meal, and in the present month, the patient has cut that back to only twice a week which indicates a trend or behavior heading in the direction of improved healthy eating habits even though they may not still be considered "healthy" eating habits. This information may be relayed to the physician via the physician interface engine 132 and/or may be the basis for performing other cognitive operations via the cognitive analysis pipelines 136.

The particular analyzer modules 112-119 perform their cognitive analysis operations with regard to specific categories of commercial transaction data and specific behaviors, habits, or trends that those analyzer modules 112-119 are specifically trained to evaluate. Thus, for example, the traveling analyzer module 112 may analyze product/service/activity information, as well as location information, present in commercial transactions to identify behaviors of the patient with regard to where the patient travels, how often they travel, what modes of transportation the patient utilizes, etc. This information may be correlated with secondary lifestyle information regarding the particular geographical regions to which the patient travels, such as nutritional information for those geographical regions, known health risk information for those regions, and the like. The nutrition habit analyzer module 114 may analyze particular food items purchased by the patient to determine the nutritional consumption behaviors of the patient. The cultural consumption analyzer module 116 may analyze commercial data identifying the patient's attendance at particular cultural events, functions, etc. The calorie consumption analyzer module 118 may perform analysis of the caloric intake of the patient to determine eating patterns of the patient. The generosity analyzer modules 119 may analyze elements of commercial transactions indicative of the patient's generosity to others and to other organizations, including tips the patient may have provided, charitable donations, etc. It should be appreciated that some aspects of lifestyle behavior, such as cultural consumption and generosity, may not have a direct biological affect on the health of the patient, but have been determined to have indirect causality to particular health conditions, e.g., patients that tend to go to particular cultural events on a regular basis have less stress or increased happiness or patients that tend to be more generous also tend to have greater happiness, leading to an overall better health of the patient. Moreover, some aspects like these may be more applicable to mental state of the patient rather than a physical biological medical state and may have greater importance when evaluating the mental medical condition of the patient.

The results of the various analysis of the analyzer modules 112 may be combined into a lifestyle behavior information output for a particular patient which may be output to the health services computing system 130. The lifestyle behavior information output may comprise categorizations of the lifestyle behaviors, patterns, habits for each type of commercial transaction data and secondary source lifestyle information determined by the analyzer modules 112-119, e.g., healthy/unhealthy nutritional habits, traveling: rare/ often/seldom, activity: active, inactive, partially active, etc. Moreover, the lifestyle behavior information output may include the underlying raw data or supporting evidence for the categorization generated by the analyzer modules 112-119. This information may be provided to the health services computing system 130 with an identifier of the patient to which the information corresponds.

Based on the identity of the patient in the lifestyle behavior information, corresponding EMR data may be retrieved for the patient from the patient EMR data 131. The health services computing system 130 may apply cognitive analysis logic, such as may be provided as part of one or more cognitive analysis pipelines 136, to the lifestyle behavior patterns, habits, or trend information and corresponding patient information from the patient EMR data 131 to determine the impact of the patient's lifestyle choices, habits, and activities on the patient's health, medical conditions, and treatments. The health services computing system 130 may present results of such cognitive analysis to the physician and/or patient via the physical interface engine 132 which comprises logic for generating a graphical user interface, warning message, notification communications, or the like, that may be accessed by a user via the client device 135 or which may be proactively transmitted to the client device 135 so as to notify the user of particular concerns regarding the patient's health, medical conditions, or treatments.

The patient EMR data 131 may be obtained from remotely located patient clinical data sources 120 and/or may be stored locally. The patient EMR data 131 may comprise various types of patient clinical data and other patient information from a variety of different source computing systems associated with health service providers, medical product providers, pharmacies, insurance companies, and the like. For example, patient EMR data 131 may comprise a collection of clinical data for a patient obtained from hospitals, doctor offices, pharmacies, medical equipment supply companies, health insurance companies, clinics, medical imaging service providers, medical laboratories, etc. In some cases, patient clinical data may also be obtained from wearable or portable health and activity monitoring devices or applications executing on portable devices, e.g., FitBit™, applications executing on portable computing devices, smartphones, or the like. The locally stored patient EMR data 131 may be previously obtained from remote sources 120 and stored locally, or may be obtained locally from medical personnel input based on patient interactions, e.g., at a doctor's office, the local patient EMR data 131 may be input via local computing device interaction by medical personnel.

The remotely located patient clinical data sources 120 may be accessed via one or more data networks (not shown in FIG. 1) to obtain patient clinical data information, which may be collected from one or more other clinical data sources (not shown) and/or collected and stored from the patient's portable health monitoring device(s). That is, the health services computing system 130 may access information stored in the remotely located patient clinical data source 140 via a network interface and provide the retrieved patient information, or a designated portion thereof to which the patient has granted access, to the health service computing system 130.

In some illustrative embodiments, the remotely located patient clinical data source 120 may be a cloud computing system comprising a plurality of computing device that share the responsibility for maintaining and protecting patient medical information, such as may be provided in one or more patient EMR data structures, obtained from one or more patient information source computing systems, such as via one or more data networks. Moreover, the remotely located patient clinical data source 120 may obtain patient information collected from the patient's portable health monitoring device(s).

The remotely located patient clinical data source 120 may store a variety of different types of clinical data 122 obtained from a variety of different clinical data sources. For example, the patient clinical data that may be collected and stored in the remotely located patient clinical data source 120 may include, for each of a plurality of patients, demographic information, allergy information, diagnosis information, vital sign information, laboratory test results information, medical procedure (operations) information, health services provider information and health insurance provider information, information regarding physical exams, pathology reports, clinical narrative notes, hospital/clinical discharge summary information, radiology reports, cardiology reports, other patient encounter information, patient genetic data (e.g., gene sequence data), or the like 124.

The patient EMR data 131, either obtained locally or remotely from the remotely located patient clinical data source 140, may be cognitively processed and analyzed, along with the lifestyle behavior pattern, habits, and trends information obtained from the commercial transaction analysis system 100, by the cognitive analysis pipeline(s) 136 of the health service computing system 130 to generate information indicative of changes in a patient's health condition, lifestyle behaviors (habits), adherence to treatments, and the like, relevant to the patient's overall health, previous medical conditions and/or treatments associated with the patient, or the like. In some illustrative embodiments, the cognitive analysis pipeline 136 may further perform cognitive operations for recommending courses of action to a medical professional for treating the patient, which may include recommending new treatments for the patient's medical condition(s), recommending modifications to existing treatments prescribed to the patient, or the like.

The cognitive analysis pipeline(s) 136 may comprise one or more cognitive analytics modules (not shown) that evaluate the received patient information (patient EMR data, clinical data, portable health monitor device captured information, and the like) as well as the lifestyle behavior patterns, habits, or trend information (collectively referred to hereafter as lifestyle pattern information), relative to the patient's overall health, previous medical conditions being treated, and the particular treatments prescribed, and may apply medical knowledge, treatment guidelines, and the like, that may be provided in electronic documents of a corpus or otherwise stored electronically for application to this patient information and lifestyle pattern information. The application of the knowledge from these medical resources to the patient information and lifestyle pattern information by the one or more cognitive analytics modules of the cognitive analysis pipeline(s) 136 provides an indication of the most relevant change information in the patient's medical condition, patient's lifestyle information (e.g., habits), and adherence to previously prescribed treatments. Moreover, in some illustrative embodiments, this change information may be used to drive further cognitive operations such that the cognitive analysis pipeline(s) 136 may generate treatment recommendations for the patient, recommended modifications to existing treatments, or even specific targeted warning messages, notifications, or the like, to be transmitted to the patient's client device or physician's client device 135.

The results generated by the analytics modules of the cognitive analysis pipeline(s) 136 may be provided to the physician interface engine 132 which generates a physician interface in which the relevant clinical data of the patient 133 as well as the relevant cognitive analysis pipeline evaluation results 134 specifying changes in the patient's medical condition, patient's lifestyle (e.g., habits), and adherence to treatments, may be provided in an accentuated manner. In the depicted example, the relevant cognitive analysis pipeline evaluation results 134 represents an evaluation and categorization of the patient's change in lifestyle behavior patterns, habits, and activities (i.e. lifestyle pattern information) since a last visit or encounter with the patient by the physician. In particular, the lifestyle pattern information evaluated in the depicted example includes nutritional lifestyle pattern information (e.g., patient has an unhealthy eating pattern), cultural lifestyle pattern information (e.g., whether the patient engages in cultural activities), travel lifestyle patterns (e.g., whether the patient travels to different geographical regions on a regular basis or not), medication lifestyle patterns (e.g., does the patient have a pattern of filling prescriptions), and activity lifestyle patterns (e.g., is the patient highly active, mildly active, or inactive).

These habits may also be evaluated based on the patient information collected from the patient's portable health monitoring device(s), which may be included in the patient EMR data 131. Thus, for example, the activity tracking capabilities, sleep monitoring capabilities, and medication reminder capabilities of the portable health monitoring devices may be used to generate patient information describing the patient's activity, sleep, and responsiveness to medication reminders which can then be evaluated by the cognitive analytics modules of the cognitive analysis pipeline(s) 136, along with the other patient EMR data and lifestyle pattern information, to determine if the patient is achieving a desired level of activity, getting good sleep, and is taking their medication.

Thus, the patient's current medical conditions, treatments, etc., may be retrieved from the EMR data 131 and corresponding relevant information that is relevant to the medical conditions, treatment, or overall health of the patient may be extracted from the lifestyle behavior information provided by the commercial transaction analysis system 100, which comprises or represents the collected commercial transaction data and secondary information as noted above. Correlations of patient EMR data 131 with the relevant health information extracted from the lifestyle behavior information, and thus the commercial transactions, may be based on the predefined categories noted above with cognitive logic being employed to identify what categories of extracted health information have an impact on particular categories of patient EMR data, medical conditions, treatments, etc. The relevant information may then be analyzed by the cognitive logic of the cognitive analysis pipeline(s) 136, in accordance with guideline information for the medical condition, treatments, or overall health of the patient, to identify the impact of the patient's lifestyle choices on the patient's medical condition, treatments, and overall health. For example, the cognitive analysis pipelines 136 may correlate increased cholesterol measurements present in patient EMR data with an unhealthy nutritional behavior pattern of the patient and an inactive activity level of the patient as identified from the analysis of the commercial transaction data.

As another example, the patient may report to the physician that they have had multiple occurrence of dizziness in the past month, and this may be recorded in the patient EMR. Moreover, the patient EMR may indicate that the patient is a type 2 diabetes patient. The patient's commercial transaction data shows that the patient has not filled their prescription for insulin in the last month and has been eating unhealthy with a high caloric intake. The combination of these factors identified by the cognitive analysis pipeline 136 which may then generate an output via the physician interface engine 132 that indicates this combination of factors as a lifestyle behavior that the physician may want to discuss with the patient. For example, the physician interface may highlight portions of the interface where the patient's nutritional habits are identified, where the patient's clinical data indicates an increase in blood sugars and the previous diagnosis of the patient as a type 2 diabetes patient, and the portion of the interface where the patient's medication behaviors indicate that the patient is not filling their insulin prescription. In some illustrative embodiments, the cognitive analysis pipelines 136 may in fact construct a natural language notification that may be output as part of the physician interface that indicates the correlations between medical conditions of the patient, treatments, and lifestyle behaviors, e.g., "Patient reports dizziness. The patient is being treated for Type 2. Diabetes. The patient has been eating unhealthy with high caloric intake and has failed to keep up with their insulin treatments."

As shown in FIG. 1, the results of the cognitive analysis of the cognitive analysis pipelines 136, as well as the clinical data and patient lifestyle behavior information, may be provided to the physician interface engine 132 which may construct a physician interface for output to a client device 138. The physician interface may comprise portions of a graphical user interface that set forth the relevant patient clinical data 133 as well as the relevant lifestyle behavior information 134. The relevance of portions of the clinical data and the lifestyle behavior information may be evaluated by the cognitive analysis pipelines 136 based on the particular medical conditions associated with the patient, the particular treatments associated with the patient, and the particular symptoms reported by the patient, based on medical knowledge obtained from medical knowledge resources (not shown), such as medical guidelines documents, physician desk references, pharmacology reference data, and the like, which may be provided in electronic form as part of a medical reference electronic corpus. Thus, in some illustrative embodiments, the physician interface generated by the physician interface engine 132 and provided to the client device 138 may comprise subsets of the clinical data obtained from the patient EMR data 131, and subsets of the lifestyle behavior information generated by the commercial transaction analysis system 100, that are relevant to the patient's medical condition, treatments, and reported symptoms. In some cases, the interface may further include subsets of such information that are generally applicable to all patients' overall health evaluation. Moreover, as noted above, the interface may present information relevant to both biological health as well as mental health.

As shown in FIG. 1, with regard to the relevant lifestyle behavior information 134, the output of this information via the physician interface may include a general evaluation of the patient's lifestyle behavior with regard to the particular category of commercial transaction data, e.g., nutrition, culture, travel, medications, activity, etc. In addition, the output of information may include a synopsis of the underlying data indicating a reason for the general evaluation, e.g., the patient's nutrition habits are unhealthy because they ate 19 burgers and 3 gallons of ice cream over the last month. Moreover, the interface may be constructed such that the physician may drill down into the information presented to obtain further detailed information as to the underlying reasoning for the general evaluation, including viewing representations of the raw data collected from commercial transaction data if desired, e.g., the physician may click on the "activity" lifestyle behavior classification and drill down into the reasoning, i.e. no commercial transactions indicating attending a gym or participating in organized physical activity.

Thus, in some illustrative embodiments, the health services computing system 130 utilizes the lifestyle behavior information to provide additional insights to a physician when evaluating a patient's medical condition, adherence to treatments, reported symptoms, as well as overall general physical and mental health. Thus, in these illustrative embodiments, the health services computing system 130 serves as a decision support system by providing insight output in an accentuated manner, potentially with constructed natural language notifications, warnings, or other messages, which aid the physician or medical professional, or even the patient themselves, in determining how to best treat the patient so as to improve their health both in general and with regard to specific medical conditions.

In other illustrative embodiments, further cognitive operations may be performed to assist physicians with treating patients that go at least one step further and present recommendations to the physician as to how to proceed with interacting with or treating the patient. For example, the health services computing system 130 may utilize the cognitive analysis pipelines 136 to generate treatment recommendations, or recommendations for modifying existing treatments, for the patient based on the correlation of the patient EMR data with the lifestyle behavior information and evaluation of relevancy to the patient's medical conditions, treatments, reported symptoms, or overall health. The cognitive analysis pipelines 136 may determine a treatment for a medical condition of the patient based on the application of medical guidelines documents and the like from a corpus and may then evaluate the patient's ability to adhere to the treatment based on their lifestyle behavior patterns. Alternatively, the cognitive analysis pipelines 136 may evaluate previously prescribed treatments and determine the areas of lifestyle behavior information where the patient is deviating from the previously prescribed treatment and determine an adjustment to bring the patient back into conformance with the prescribed treatment, e.g., increase activity by getting a gym membership and using it, reducing calorie intake by being on a low fat diet, etc. These recommendations may be generated through cognitive analysis by the cognitive analysis pipelines 136 and presented to the physician or other medical personnel via the physician interface generated by the physician interface engine 132.

Thus, based on the results of the analysis of the patient EMR data and lifestyle behavior information, the physician interface may be generated by the physician interface engine 132, which may include warnings, notifications, and the like to the physician so that the physician can communicate with the patient or otherwise provide awareness to the physician when interacting with the patient as part of the physician's treatment of the patient. In addition, the commercial transaction data can be analyzed to see whether there are any special areas of concern, such as instances of transactions that occurred in different geographic regions which may cause urgent concerns (e.g., ingesting foods in a geographical region known to have parasites present in the food supply, traveling to a geographical region where there is a known disease outbreak, etc.) or otherwise may have an impact on the patient's health. For example, if a patient travels to a place where there is a high level of risk for a disease or infection, this information can be retrieved to provide relevant background for better understanding the patient's health. Such information may be used to both identify negative factors, e.g., higher level of risk of a disease or infection, as well as positive factors, such as traveling in different regions where the food is made in a relatively healthy fashion. For example, even though the name of the food or dish is still the same between regions, in one particular region the food or dish may be known to be prepared with relatively less oil, sodium and sugar being added, indicating a lower negative health impact or even a greater beneficial impact on the patient's health.

It should be appreciated that while the commercial transaction analysis system 100 is shown as separate from the health services computing system 130, the illustrative embodiments are not limited to such. Rather, in some embodiments, the commercial transaction analysis system 100 may be provided in the health services computing system 130 and may be integrated in, or work in conjunction with, the cognitive analysis pipelines 136 and/or physician interface engine 132.

The physician interface provided by the physical interface engine 132 may be provided to the client device 138 for output such that a physician, or other medical personnel, may access the interface and view the most relevant information for the patient prior to encountering, or during an encounter with, the patient. As noted above, the information output in the physician interface may be specifically customized to the particular patient's previous medical conditions currently being treated, such as may be indicated in the patient's previous EMR data from a previous visit or encounter, the previously prescribed treatments that the patient should be adhering to for the medical conditions, as well as the reason for the patient's current visit or encounter, e.g., reported symptoms. Hence, the output of the physician interface provides information to the physician that is relevant to the current visit or encounter between the physician and the patient and includes information gathered and evaluated automatically from commercial transactions that the patient has engaged in. The presentation of the evaluation results and the relevant clinical data and lifestyle behavior information is such that the most important aspects of the patient's medical condition, changes in lifestyle, and adherence to treatments are accentuated for further inquiry by the physician when treating the patient, thereby assisting with decision support operations and/or interacting with the patient during a patient encounter.

Figure 2:
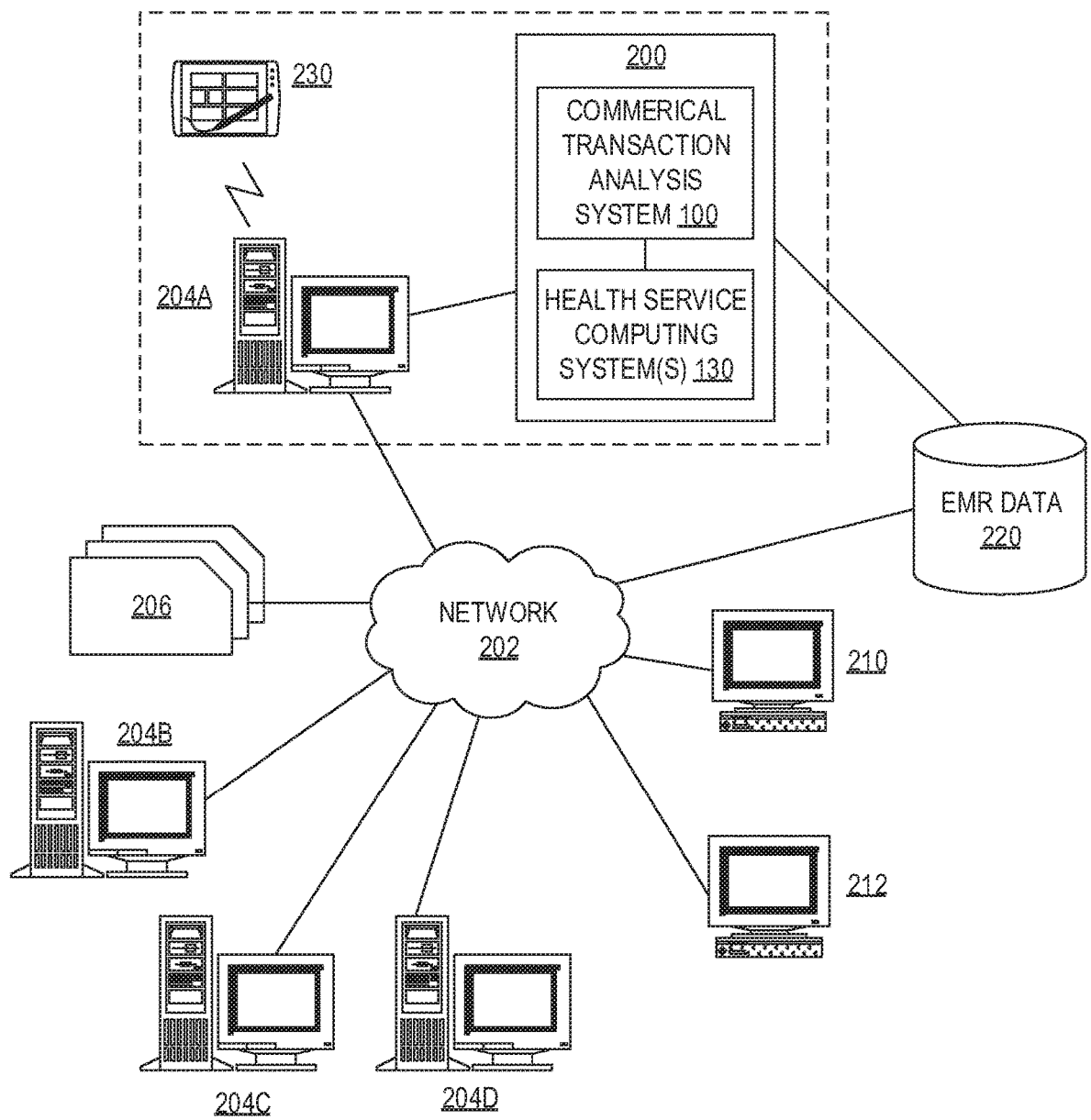
FIG. 2 is an example diagram of a distributed data processing system in which aspects of the present invention may be implemented.
Figure 3:
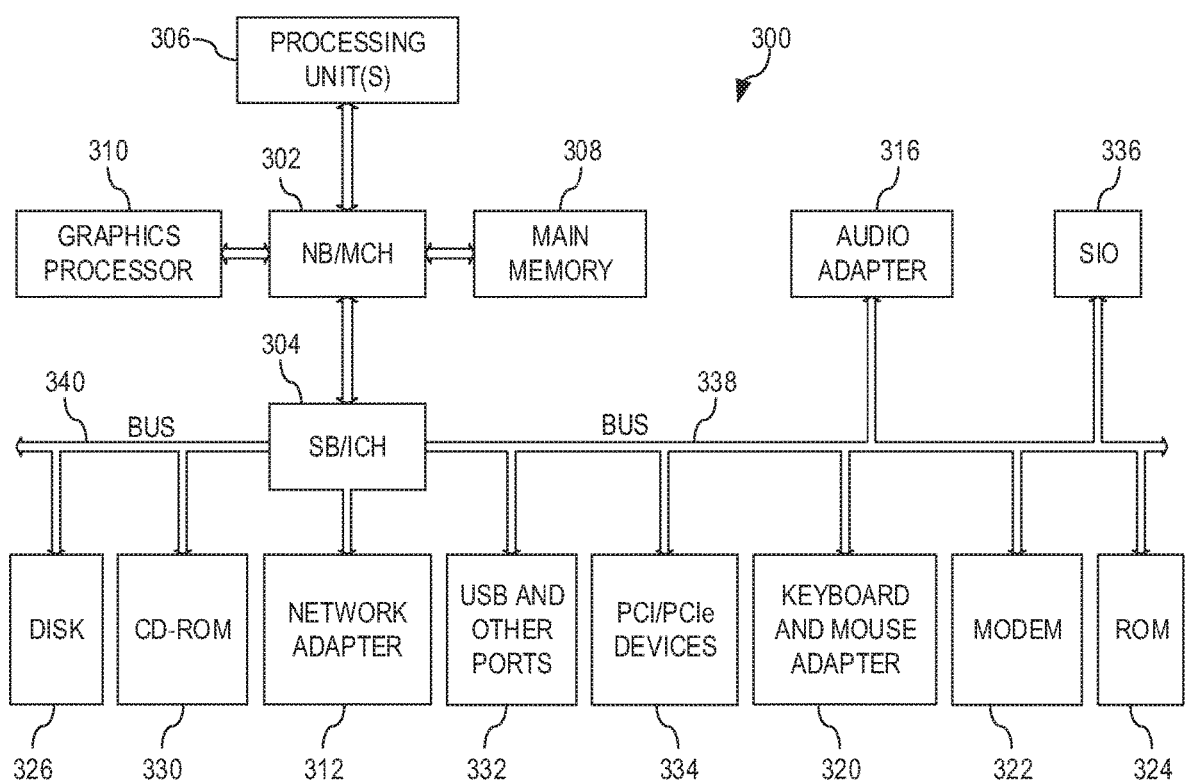
FIG. 3 is a block diagram of an example data processing system in which aspects of the illustrative embodiments are implemented.

It should be appreciated that the illustrative embodiments may be utilized in many different types of data processing environments. In order to provide a context for the description of the specific elements and functionality of the illustrative embodiments, FIGS. 2-3 are provided hereafter as example environments in which aspects of the illustrative embodiments may be implemented. It should be appreciated that FIGS. 2-3 are only examples and are not intended to assert or imply any limitation with regard to the environments in which aspects or embodiments of the present invention may be implemented. Many modifications to the depicted environments may be made without departing from the spirit and scope of the present invention.

FIGS. 2-3 are directed to describing an example cognitive system for healthcare applications which implements a request processing apparatus, request processing methodology, and request processing computer program product with which the mechanisms of the illustrative embodiments are implemented. In particular, the cognitive system may comprise a commercial transaction analysis system 100 and a health services computing system 130 which operate in conjunction to obtain and analyze commercial transaction data from commercial transaction data sources and provide cognitive evaluations of the commercial transaction data gathered from such commercial transaction data sources, secondary lifestyle information from secondary sources, and patient EMR data from clinical data sources, to evaluate a patient's medical condition, lifestyle behavior (e.g., habits), and adherence to treatments, which may include evaluations with regard to changes in such since a last visit or encounter between the physician and the patient. This functionality may be performed periodically, according to a predetermined schedule, or in response to the detection of particular events. For example, the functionality may be performed responsive to the receiving of new commercial transaction data from commercial transaction data sources on a periodic or scheduled basis, or in response to a user triggering retrieval of such commercial transaction data, such as in response to a physician requesting to view a particular patient's EMR data which may in turn trigger the commercial transaction analysis system 100 retrieving commercial transaction data for the specified patient from commercial transaction data sources and performing the various analysis as described previously with regard to FIG. 1. A physician interface may then be generated for viewing by the physician or other medical personnel either during, or prior to, the physician encountering the patient.

The commercial transaction analysis system 100 of the cognitive health system 200 may implement one or more cognitive analytics modules, such as cognitive analytics modules 112-119 in FIG. 1, which themselves may utilize request processing pipelines to perform evaluations of commercial transaction data with regard to the particular configured analytics that the particular analytics module 112-119 is to perform. It should be appreciated that the cognitive analytics modules 112-119 may utilize a request processing pipeline that is separately trained and/or configured to process commercial transaction data associated with different domains. For example, in some cases, a first request processing pipeline of a first analytics module 112 may be trained to operate on commercial transaction data with regard to a travel purchases while another request processing pipeline may be trained to operate on commercial transaction data with regard to food purchases, and yet another based on commercial transaction data corresponding to cultural or generosity information. Moreover, each request processing pipeline of each of the cognitive analytics modules 120 may have their own associated corpus or corpora of secondary lifestyle information comprises electronic documents and data structures of secondary sources, e.g., secondary sources of lifestyle information 150 in FIG. 1, that they ingest and operate on.

As an overview, a cognitive system, or cognitive analytics module 112-119 and/or cognitive analysis pipelines 136, is a specialized module configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware.

IBM Watson™ is an example of one such cognitive system which can process human readable language and identify inferences between text passages with human-like high accuracy at speeds far faster than human beings and on a larger scale. The cognitive system, e.g., IBM Watson™, may be used to provide cognitive analytics modules 112-119 and/or cognitive analysis pipelines 136, which are configured specifically to perform analytics evaluations on various commercial transaction data, lifestyle behavior information, patient EMR data, and/or the like. In particular, the cognitive analytics modules 112-119 may cognitively analyze the commercial transaction data categorized into categories of commercial transaction data for which they are specifically trained to operate on and generate lifestyle behavior information representing the lifestyle behavior patterns, habits, and trends represented by the patient's commercial transactions. The cognitive analysis pipelines 136 are trained to cognitively correlate and analyze patient EMR data and lifestyle behavior information from the commercial transaction analysis system 100 to identify relevant portions of such data to the health of a particular patient, the medical conditions of that patient, and the treatments of that patient, and present results of such analysis indicating the positive/negative aspects of the relevant information in an accentuated manner for use in generating a physician interface. In some illustrative embodiments, the cognitive analysis pipelines 136 are further configured and trained to specifically generate treatment recommendations or recommendations for modifications in prescribed treatments for the patient based on the cognitive analysis of patient EMR data and lifestyle behavior information.

As shown in FIG. 2, the cognitive health system 200, comprising the commercial transaction analysis system 100 and the health services computing system(s) 130, is implemented on one or more computing devices 204A-D (comprising one or more processors and one or more memories, and potentially any other computing device elements generally known in the art including buses, storage devices, communication interfaces, and the like) connected to the computer network 202. For purposes of illustration only, FIG. 2 depicts the cognitive health system 200 being implemented on computing device 204A only, but as noted above the cognitive health system 200 may be distributed across multiple computing devices, such as a plurality of computing devices 204A-D. The network 202 includes multiple computing devices 204A-D, which may operate as server computing devices, and client computing devices 210-212, in communication with each other and with other devices or components via one or more wired and/or wireless data communication links, where each communication link comprises one or more of wires, routers, switches, transmitters, receivers, or the like.

In some illustrative embodiments, the cognitive health system 200 and network 202 enable automatic extraction and cognitive analysis of lifestyle behavior pattern, habit, and trend information from commercial transaction data obtained from commercial transaction data sources to generate indications of the patient's lifestyle which may be important to an evaluation of the patient's overall health, medical conditions, and adherence to prescribed treatments. As described previously, the commercial transaction analysis system 100 in combination with the health service computing system 130 may also operate on stored EMR data and clinical data for the patient 220, which may be locally stored or remotely stored on other computing systems or network attached data storage that is accessible by the cognitive health system 200, as well as medical knowledge obtained from medical knowledge resources, such as may be provided in one or more corpora 206. For example, the cognitive health system 130 may access a corpus or corpora of electronic documents 206 via the network 202, where portions of the corpus or corpora 206 may be provided on one or more server computing devices, network attached storage devices, in one or more databases, or other computing devices not explicitly shown in FIG. 2. The network 202 includes local network connections and remote connections in various embodiments, such that the cognitive health system 200 may operate in environments of any size, including local and global, e.g., the Internet.

The electronic documents of the one or more corpora 206 may include any file, text, article, or source of data for use in the cognitive health system 200 and may be provided in a structured or unstructured manner, e.g., natural language documents which may be processed using natural language processing to extract medical knowledge, treatment characteristics, and the like. For example, the electronic documents of the one or more corpora 206 may comprise medical knowledge bases, medical condition diagnosis knowledge sources, treatment guidelines, and the like, that specify various knowledge, criteria, and characteristics of medical conditions and treatments for such medical conditions. This information may be correlated with the medical conditions and treatments associated with the patient. This information may be used to determine what portions of the lifestyle behavior information output by the commercial transaction analysis system 100 is relevant to patient health, medical conditions, or treatments. The EMR data and lifestyle behavior information may further be evaluated based on this knowledge obtained from the one or more corpora 206 to determine what criteria are met or not met, what certain ranges of values may represent, what portions of treatments are satisfied and what consequences may occur based on a failure to satisfy certain portions of the treatments, etc., as well as lifestyle behaviors, i.e. behavior patterns, habits, or trends, that are contributing positively/negatively to the patient's overall health, particular medical conditions, and/ or particular treatments. This information may be used to identify relevant changes in patient medical condition, patient lifestyle (e.g., habits), and treatment adherence that are to be accentuated in a physician interface, as discussed previously.

The physician interface may be provided to, or otherwise accessed, by a physician or other medical personnel via a client computing device 230. In the depicted example, the client computing device is a portable tablet type computing device 230 which has graphical display capabilities used to provide a graphical user interface output of the physician interface. The output on the client device 230 may comprise patient clinical data and relevant lifestyle behavior information as noted previously. The physician interface displays the information gathered and evaluated by the cognitive analytics modules of the commercial transaction analysis system 100, the relevant clinical data retrieved from patient EMRs, and/or the results of cognitive analysis by one or more cognitive analysis pipelines 136, to identify the relevant aspects of the clinical data and lifestyle behavior information for the patient's health, medical conditions, and treatments. Moreover, the physician interface may display the correlations of such information in a way as to explain the determined impact and interaction of the patient's lifestyle behavior information with the clinical data and the patient's health, medical conditions, and adherence to treatments, as previously described above. It should be appreciated that the cognitive analytics modules of the commercial transaction analysis system 100 and the cognitive analysis pipelines 136 may apply thresholds, logic functions, and the like, to determine a degree or level of relevance or importance which may be used to identify an accentuation or particular representation of the information in the physician's interface and thereby direct the physician's attention to this information. In this way, the most relevant clinical data and lifestyle behavior information is made apparent to the physician, medical personnel, or even patient, based on the most current knowledge of the patient's medical condition, lifestyle, and treatment adherence as determined automatically from commercial transaction data and patient EMR data.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 3 is provided as an example of one type of data processing system in which aspects of the present invention may be implemented. Many other types of data processing systems may be likewise configured to specifically implement the mechanisms of the illustrative embodiments.

FIG. 3 is a block diagram of an example data processing system in which aspects of the illustrative embodiments are implemented. Data processing system 300 is an example of a computer, such as server 204 or client 210 in FIG. 2, in which computer usable code or instructions implementing the processes for illustrative embodiments of the present invention are located. In one illustrative embodiment, FIG. 3 represents a server computing device, such as a server 204, which implements a cognitive system 200 that includes the mechanisms of the illustrative embodiments described herein.

In the depicted example, data processing system 300 employs a hub architecture including North Bridge and Memory Controller Hub (NB/MCH) 302 and South Bridge and Input/Output (I/O) Controller Hub (SB/ICH) 304. Processing unit 306, main memory 308, and graphics processor 310 are connected to NB/MCH 302. Graphics processor 310 is connected to NB/MCH 302 through an accelerated graphics port (AGP).

In the depicted example, local area network (LAN) adapter 312 connects to SB/ICH 304. Audio adapter 316, keyboard and mouse adapter 320, modem 322, read only memory (ROM) 324, hard disk drive (HDD) 326, CD-ROM drive 330, universal serial bus (USB) ports and other communication ports 332, and PCI/PCIe devices 334 connect to SB/ICH 304 through bus 338 and bus 340. PCI/PCIe devices may include, for example, Ethernet adapters, add-in cards, and PC cards for notebook computers. PCI uses a card bus controller, while PCIe does not. ROM 324 may be, for example, a flash basic input/output system (BIOS).

HDD 326 and CD-ROM drive 330 connect to SB/ICH 304 through bus 340. HDD 326 and CD-ROM drive 330 may use, for example, an integrated drive electronics (IDE) or serial advanced technology attachment (SATA) interface. Super I/O (SIO) device 336 is connected to SB/ICH 304.

An operating system runs on processing unit 306. The operating system coordinates and provides control of various components within the data processing system 300 in FIG. 3. As a client, the operating system is a commercially available operating system such as Microsoft® Windows 10°. An object-oriented programming system, such as the Java™ programming system, may run in conjunction with the operating system and provides calls to the operating system from Java™ programs or applications executing on data processing system 300.

As a server, data processing system 300 may be, for example, an IBM® eServer™ System p° computer system, running the Advanced Interactive Executive) (AIX®) operating system or the LINUX® operating system. Data processing system 300 may be a symmetric multiprocessor (SMP) system including a plurality of processors in processing unit 306. Alternatively, a single processor system may be employed.

Instructions for the operating system, the object-oriented programming system, and applications or programs are located on storage devices, such as HDD 326, and are loaded into main memory 308 for execution by processing unit 306. The processes for illustrative embodiments of the present invention are performed by processing unit 306 using computer usable program code, which is located in a memory such as, for example, main memory 308, ROM 324, or in one or more peripheral devices 326 and 330, for example.

A bus system, such as bus 338 or bus 340 as shown in FIG. 3, is comprised of one or more buses. Of course, the bus system may be implemented using any type of communication fabric or architecture that provides for a transfer of data between different components or devices attached to the fabric or architecture. A communication unit, such as modem 322 or network adapter 312 of FIG. 3, includes one or more devices used to transmit and receive data. A memory may be, for example, main memory 308, ROM 324, or a cache such as found in NB/MCH 302 in FIG. 3.

Those of ordinary skill in the art will appreciate that the hardware depicted in FIGS. 2 and 3 may vary depending on the implementation. Other internal hardware or peripheral devices, such as flash memory, equivalent non-volatile memory, or optical disk drives and the like, may be used in addition to or in place of the hardware depicted in FIGS. 2 and 3. Also, the processes of the illustrative embodiments may be applied to a multiprocessor data processing system, other than the SMP system mentioned previously, without departing from the spirit and scope of the present invention.

Moreover, the data processing system 300 may take the form of any of a number of different data processing systems including client computing devices, server computing devices, a tablet computer, laptop computer, telephone or other communication device, a personal digital assistant (PDA), or the like. In some illustrative examples, data processing system 300 may be a portable computing device that is configured with flash memory to provide non-volatile memory for storing operating system files and/or user-generated data, for example. Essentially, data processing system 300 may be any known or later developed data processing system without architectural limitation.

Figure 4:
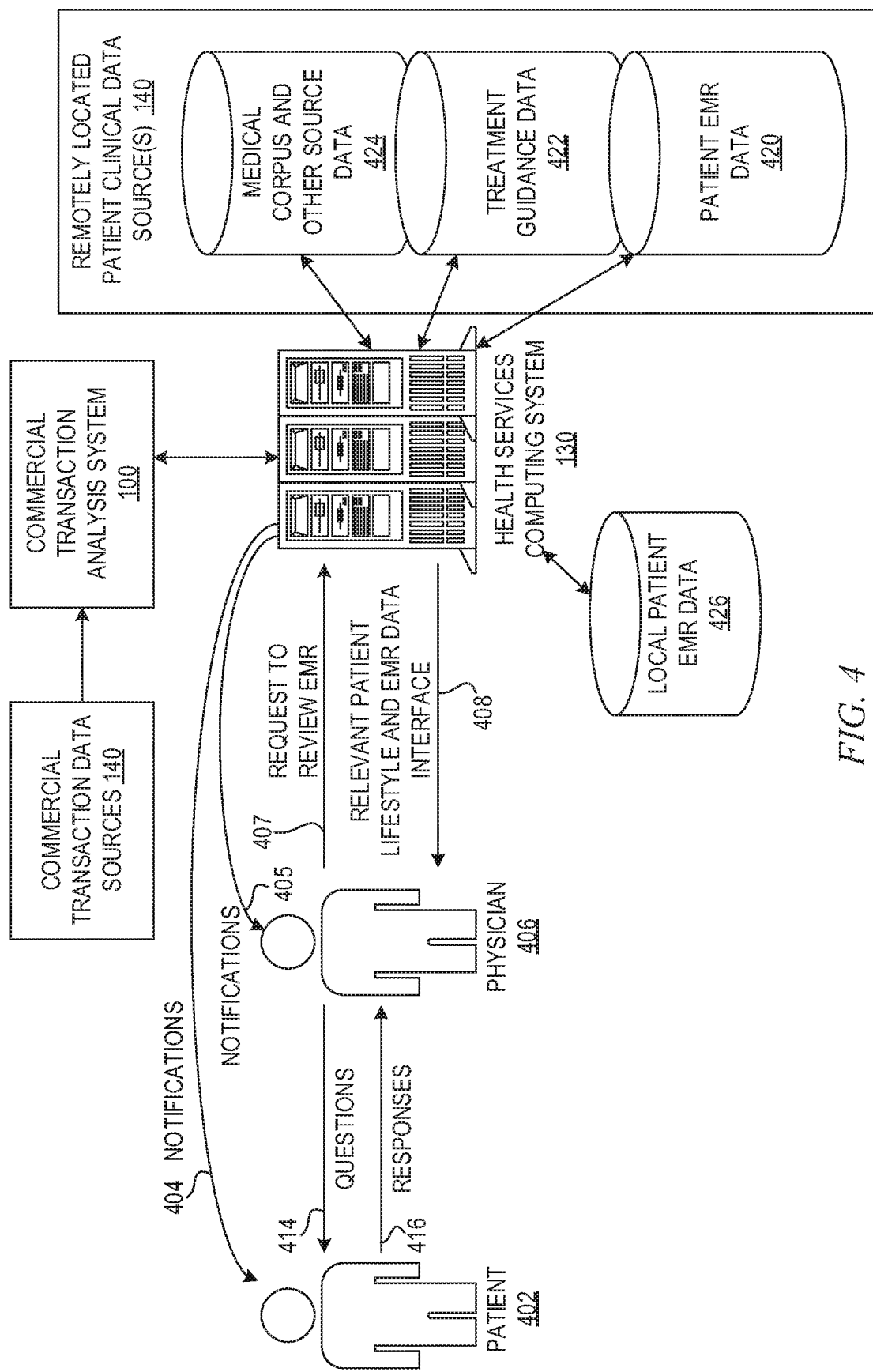
FIG. 4 is an example diagram illustrating an interaction of elements of a healthcare cognitive system in accordance with one illustrative embodiment.

FIG. 4 is an example diagram illustrating an interaction of elements of a healthcare cognitive system in accordance with one illustrative embodiment. The example diagram of FIG. 4 depicts an implementation of a healthcare cognitive system that is configured to provide decision support services to a physician in the way of cognitive evaluation of patient information collected from patient EMR data and also automatic extraction and analysis of patient lifestyle behavior patterns, habits, and trends from commercial transaction data, as performed by the commercial transaction analysis system 100. The results of such evaluation may be presented to the physician 406 prior to, or commensurate with, the physician 406 encountering the patient 402, such as in an exam room. The results of the evaluation take into account the most up-to-date and relevant lifestyle behavior information relevant to the particular patient's medical conditions, treatments, and/or reported symptoms and aids the physician or other medical personnel, or even the patient themselves, in understanding the impact of the patient's lifestyle choices on their overall health, medical conditions, and treatments. These functions may be performed in an automated manner without requiring the patient to actively report such information and without requiring the physician to obtain the information from the patient through an encounter.

As shown in FIG. 4, the commercial transaction analysis system 100 may obtain commercial transaction data from commercial transaction data sources 140. This may be done automatically at periodic times, according to a schedule, or in response to a particular defined event. For example, in one illustrative embodiment, in response to the physician 406 requesting to view a particular patient 402 EMR data, the request to review the EMR 407 may trigger the health services computing system 130 sending a request to the commercial transaction analysis system 100 to retrieve commercial transaction data for the patient from the data sources 140 and analyze it to provide lifestyle behavior information to be processed by the health services computing system 130, such as for use in presenting a physician interface to the physician 406. The request to review the patient 402 EMR data, i.e. request 407, may initiate a lookup of the patient EMR data (e.g., clinical data) in local patient EMR data storage 426, remotely located patient EMR data storage 420, or the like, and may identify any previously specified permissions associated with the patient. Moreover, the health services computing system 130 may also identify previous medical conditions for which the patient is being treated and the particular previously prescribed treatments.

This information may be used to correlate with patient lifestyle behavior information of the patient as generated automatically by the commercial transaction analysis system 100 based on its cognitive analysis of commercial transactions engaged in by the patient as reported by the commercial transaction data sources. In particular, the patient's behavior patterns, habits, and trends with regard to their purchases of products/services/activities is determined and analyzed to provide lifestyle behavior information to the health services computing system 130 for processing as previously described above. The correlation and analysis may include cognitive analysis pipeline operations that apply knowledge gathered from the ingestion of medical corpus and other source data 424, treatment guidance data 422, and other remotely located patient clinical data sources 140 and the like. The results of the cognitive analysis performed by the commercial transaction analysis system 100 and health services computing system 130 may be utilized to generate notifications 404, 405 which may be sent to the patient and/or physician, or to generate a physician interface 408 such as in the manner previously described above with regard to FIG. 1, for example. The resulting physician interface 408 setting forth relevant patient lifestyle and EMR data may be used by the physician 406 to target the physician's interaction with the patient 402 via a question/response exchange 414, 416 so as to tailor the encounter with the patient 402 to the most up-to-date understanding of the patient's lifestyle as it contributes to the patient's overall health, specific medical conditions, and treatments.

That is, from the patient EMR data 420, 426, the medical conditions and the current treatments that the patient 402 may be undergoing, may be identified. The corresponding lifestyle behavior information identified and/or generated by the commercial transaction analysis system 100 based on commercial transaction data obtained from commercial transaction data sources 140, that is relevant to the current treatments and/or medical conditions, may be identified and correlated with previous version of this information to identify changes in the information, e.g., changes in the patient's lifestyle behavior. The most up-to-date information and indications of lifestyle behavior and/or changes in lifestyle behavior may be reflected in a notification or physician interface 408 presented to the physician 406 via the physician system 130 in association with the patient's EMR data when the physician 406 is viewing this information. Similarly, a determination of the reason for the patient's visit may be identified from an appointment system (a subsystem of the health services computing system 130, for example), which may include an indicator of the medical condition(s) for which the patient 402 is seeking treatment. This information may be correlated with information indicative of the important patient characteristics and health information for treating the medical condition(s), as may be obtained from medical guidelines, clinical guidance from subject matter experts, and the like, which may be stored as data structures in one or more resource data sources 422, 424. This information may then be used to select health information from the patient EMRs, and lifestyle behavior information from the automatic extraction and analysis performed by the commercial transaction analysis system 100, that are relevant to the reasons for the patient's visit which may then be identified in a notification or physician interface 408 output to the physician 406 via the health services computing system 130.

Such presentation of the notification to the physician 406 may be specifically in response to the physician 406 requesting 507 access to the patient's EMR data. Moreover, based on the presentation of the notification, e.g., the physician's interface 408, the physician 406 may review the patient's relevant lifestyle behavior information and clinical data prior to encountering the patient 402. Thereafter, the physician 406 may then conduct an encounter with the patient 402 via questions 414 and responses 416 based on the lifestyle behavior information and clinical data presented to the physician 406 via the notification, or physician's interface 408.

It should be appreciated that while FIG. 4 depicts the patient 402 and user 406 as human figures, the interactions with and between these entities may be performed using computing devices, medical equipment, and/or the like, such that entities 402 and 406 may in fact be computing devices, e.g., client computing devices. For example, the interactions 414 and 416 between the patient 402 and the user 406 may be performed orally, e.g., a physician interviewing a patient, and may involve the use of one or more medical instruments, monitoring devices, or the like, to collect information that may be input to the health services computing system 130 as patient attributes 418. Interactions between the user 406 and the health services computing system 130 will be electronic via a user computing device (not shown), such as a client computing device, portable computing device, or the like, communicating with the health services computing system 130 via one or more data communication links and potentially one or more data networks.

FIG. 5 is a flowchart outlining an example operation of a commercial transaction analysis system in accordance with one illustrative embodiment. As shown in FIG. 5, the operation starts by initiating analysis of commercial transactions to extract lifestyle information, e.g., information about products/services/activities purchased or engaged in (step 510). The commercial transactions are correlated with a patient identifier associated with the commercial transactions so as to identify the particular commercial transactions that are associated with the particular patients (step 520). The commercial transactions are analyzed to identify the products/services purchased and/or the activities engaged in (step 530). The products/services/activities are then categorized into predefined categories of types of products/services/activities (step 540). Is should be noted that the predefined categories are those that are specifically associated with aspects of products/services/activities that have a relevance to a patient's overall health or specific medical conditions/treatments.

Secondary source lifestyle information corresponding to the categories of the products/services/activities identified in the commercial transactions is retrieved (step 550). The products/services/activities identified as part of the commercial transactions conducted by the patient are analyzed with regard to the categories and the secondary source information to determine beneficial/non-beneficial health classifications of these products/services/activities with regard to patient health (step 560). Lifestyle behavior patterns/trends/habits are identified based on historical commercial transaction data along with the currently obtained commercial transaction data and the classifications (step 570).

Patient EMR data for the patient identified in the commercial transactions is retrieved, where this patient EMR data specifies various characteristics of the patient including the medical conditions of the patient and the previously prescribed treatments for this patient (step 580). The analysis results of the lifestyle information to identify lifestyle behavior patterns, habits, and trends (lifestyle behavior information) extracted from commercial transaction data is correlated with the patient EMR information based on cognitive logic and categories to identify relevant lifestyle behavior information affecting the particular patients health, medical conditions, and treatments (step 590). Based on this correlation, the changes in the patient's health, habits, and adherence to treatment may be cognitively evaluated (step 600) and relevant patient information regarding such changes since a last encounter between the patient and the physician may be identified, along with habit and treatment adherence information, and presented to a physician and/or the patient based on the correlations and evaluations (step 610). A physician interface with relevant lifestyle information and patient EMR information accentuated may then be output to the physician for use in encountering and treating the patient (step 620). The operation then terminates.

Thus, the illustrative embodiments provide mechanisms for automatically and proactively collecting commercial transaction information for commercial transactions engaged in by a patient, and automatically extracting lifestyle behavior information from such commercial transactions by identifying products/services purchased and/or activities engaged in. This information may be evaluated along with patient EMR data to identify the ways in which the patient's lifestyle choices may be positively/negatively impacting the patient's overall health, specific medical conditions, and/or previously prescribed treatments. Moreover, in some cases, this information may be used as a basis for performing other cognitive operations, such as treatment recommendation and/or treatment modification recommendations. As a result, the physician is presented with accurate information upon which the physician can base an encounter with the patient. These operations may be performed automatically without requiring the patient to proactively provide the information and may be presented to the physician prior to, or commensurate with, the physician's encounter with the patient. Moreover, in cases where an urgent situation is determined to exist based on the commercial transaction data, e.g., outbreak of an infection in a geographical region where the patient appears to have traveled, warnings and notifications may be automatically generated and transmitted on a prioritized basis.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a cognitive medical decision support system, wherein the cognitive medical decision support system operates to:

configure and train each of a plurality of lifestyle behavior pattern analyzers, by performing a machine learning process on a first set of commercial transaction data to learn weightings of lifestyle behavior factors present in the commercial transaction data relative to one another, to categorize a lifestyle behavior according to a predetermined set of lifestyle behavior pattern categories, and wherein each lifestyle data pattern analyzer is configured and trained by the machine learning process to identify patterns of data in commercial transactions indicative of lifestyle behavior patterns for a corresponding different category of commercial transaction data elements in commercial transaction data;

analyze, by artificial intelligence logic of the cognitive medical decision support system, a set of commercial transaction data structures defining a second set of commercial transactions executed by a patient to identify commercial transaction data elements corresponding to at least one of products or services purchased during each commercial transaction, or an activity, associated with the commercial transaction, engaged in by the patient;

determine, by the configured and trained plurality of lifestyle behavior pattern analyzers, a lifestyle behavior pattern of the patient based on detected patterns of commercial transaction data elements corresponding to at least one of products, services, or activities associated with the commercial transactions in the second set of commercial transactions;

evaluate, by the artificial intelligence logic of the cognitive medical decision support system, an impact of the lifestyle behavior pattern on at least one of a specific medical condition of the patient or a specific previously prescribed treatment of the patient, wherein the evaluation comprises processing the lifestyle behavior pattern of the patient, determined by the plurality of lifestyle behavior pattern analyzers, and patient electronic medical record data indicating at least one of the specific medical condition or specific previously prescribed medical treatment, through at least one cognitive analysis pipeline implementing the artificial intelligence logic of the cognitive medical decision support system; and output, by the cognitive medical decision support system, a notification indicating the impact of the lifestyle behavior pattern.

2. The method of claim 1, further comprising determining, by the cognitive medical decision support system, at least one recommendation for treating the patient based on the determined impact of the lifestyle behavior pattern, wherein the at least one recommendation comprises at least one of a recommended modification to a previously prescribed treatment or a recommendation of a new treatment to be prescribed to the patient.

3. The method of claim 1, wherein determining the impact of the lifestyle behavior pattern further comprises:
analyzing, by the cognitive medical decision support system, electronic medical records (EMRs) of a patient to identify a current treatment being performed to treat a medical condition associated with the patient;
categorizing, by the cognitive medical decision support system, each product, service, or activity, associated with commercial transactions in the set of commercial transactions, into one or more of a set of predefined categories; and
determining, by the cognitive medical decision support system, whether one or more of the products, services, or activities has been categorized into one or more predefined categories that conflict with the current treatment being performed to treat the medical condition of the patient.

4. The method of claim 3, further comprising responsive to one or more of the products, services, or activities being categorized into one or more of the predefined categories that conflicts with the current treatment being performed to treat the medical condition of the patient, outputting the notification comprises outputting, by the cognitive medical decision support system, a notification indicating that a product, service, or activity categorized into the one or more predefined categories that conflicts with the current treatment being performed to treat the medical condition of the patient impacts the current treatment.

5. The method of claim 4, wherein the warning or the notification is output to medical personnel responsible for the current treatment being performed by the patient.

6. The method of claim 1, wherein determining a lifestyle behavior pattern of the patient based on the products, services, or activities associated with the commercial transactions in the set of commercial transactions further comprises:
retrieving secondary source lifestyle information, from at least one secondary source lifestyle information source computing system, corresponding to the products, services, or activities associated with the commercial transactions, wherein the secondary source lifestyle information provides detailed health information about the particular products, services, or activities;
categorizing the products, services, or activities according to categorizations of the products, services or activities as being beneficial or non-beneficial to the health of the patient based on the detailed health information provided by the secondary source lifestyle information; and
determining the lifestyle behavior pattern based on the categorization of the products, services, or activities.

7. The method of claim 1, wherein the set of commercial transactions are executed using one or more purchasing means that are registered by the patient with the cognitive medical decision support system.

8. The method of claim 7, wherein the purchasing means comprises at least one of a credit card account identifier, a debit card identifier, an account identifier of an account associated with a provider of products, services, or activities, or a loyalty program identifier associated with a loyalty program of a provider of products, services, or activities.

9. The method of claim 1, wherein information for the set of commercial transactions is obtained from at least one of a computing system associated with a financial institution with which the patient has a relationship or one or more computing systems associated with commercial establishments with which the commercial transaction is associated.

10. The method of claim 1, wherein evaluating, by the cognitive medical decision support system, the impact of the lifestyle behavior pattern further comprises:
correlating, by the cognitive medical decision support system, the lifestyle behavior pattern with portions of an electronic medical record (EMR) for the patient based on categories of lifestyle behavior pattern information and categories of EMR information;
cognitively evaluating, by the cognitive medical decision support system, the correlations of categories of lifestyle behavior pattern information and categories of EMR information to identify changes in patient health, habits, or adherence to a prescribed treatment; and
identifying, by the cognitive medical decision support system, relevant patient information regarding changes since a last encounter between medical personnel and the patient based on the correlations, wherein the notification comprises an indication of the relevant patient information.

11. A computer program product comprising a computer readable storage medium having a computer readable program stored therein, wherein the computer readable program, when executed on a computing device, causes the computing device to implement a cognitive medical decision support system which operates to:
configure and train each of a plurality of lifestyle behavior pattern analyzers, by performing a machine learning process on a first set of commercial transaction data to learn weightings of lifestyle behavior factors present in the commercial transaction data relative to one another, to categorize a lifestyle behavior according to a predetermined set of lifestyle behavior pattern categories, and wherein each lifestyle data pattern analyzer is configured and trained by the machine learning process to identify patterns of data in commercial transactions indicative of lifestyle behavior patterns for a corresponding different category of commercial transaction data elements in commercial transaction data;
analyze, by artificial intelligence logic of the cognitive medical decision support system, a set of commercial transaction data structures defining a second set of commercial transactions executed by a patient to identify commercial transaction data elements corresponding to at least one of products or services purchased during each commercial transaction, or an activity, associated with the commercial transaction, engaged in by the patient;
determine, by the configured and trained plurality of lifestyle behavior pattern analyzers, a lifestyle behavior pattern of the patient based on detected patterns of commercial transaction data elements corresponding to at least one of products, services, or activities associated with the commercial transactions in the second set of commercial transactions;

evaluate, by the artificial intelligence logic of the cognitive medical decision support system, an impact of the lifestyle behavior pattern on at least one of a specific medical condition of the patient or a specific previously prescribed treatment of the patient, wherein the evaluation comprises processing the lifestyle behavior pattern of the patient, determined by the plurality of lifestyle behavior pattern analyzers, and patient electronic medical record data indicating at least one of the specific medical condition or specific previously prescribed medical treatment, through at least one cognitive analysis pipeline implementing the artificial intelligence logic of the cognitive medical decision support system; and output a notification indicating the impact of the lifestyle behavior pattern.

12. The computer program product of claim 11, wherein the computer readable program further causes the cognitive medical decision support system to determine at least one recommendation for treating the patient based on the determined impact of the lifestyle behavior pattern, wherein the at least one recommendation comprises at least one of a recommended modification to a previously prescribed treatment or a recommendation of a new treatment to be prescribed to the patient.

13. The computer program product of claim 11, wherein the computer readable program further causes the cognitive medical decision support system to determine the impact of the lifestyle behavior pattern further at least by:
analyzing, by the cognitive medical decision support system, electronic medical records (EMRs) of a patient to identify a current treatment being performed to treat a medical condition associated with the patient;
categorizing, by the cognitive medical decision support system, each product, service, or activity, associated with commercial transactions in the set of commercial transactions, into one or more of a set of predefined categories; and
determining, by the cognitive medical decision support system, whether one or more of the products, services, or activities has been categorized into one or more predefined categories that conflict with the current treatment being performed to treat the medical condition of the patient.

14. The computer program product of claim 13, wherein the computer readable program further causes the cognitive medical decision support system to output, responsive to one or more of the products, services, or activities being categorized into one or more of the predefined categories that conflicts with the current treatment being performed to treat the medical condition of the patient, the notification indicating that a product, service, or activity categorized into the one or more predefined categories that conflicts with the current treatment being performed to treat the medical condition of the patient impacts the current treatment.

15. The computer program product of claim 11, wherein the computer readable program further causes the cognitive medical decision support system to determine a lifestyle behavior pattern of the patient based on the products, services, or activities associated with the commercial transactions in the set of commercial transactions at least by:
retrieving secondary source lifestyle information, from at least one secondary source lifestyle information source computing system, corresponding to the products, services, or activities associated with the commercial transactions, wherein the secondary source lifestyle information provides detailed health information about the particular products, services, or activities;
categorizing the products, services, or activities according to categorizations of the products, services or activities as being beneficial or non-beneficial to the health of the patient based on the detailed health information provided by the secondary source lifestyle information; and
determining the lifestyle behavior pattern based on the categorization of the products, services, or activities.

16. The computer program product of claim 11, wherein the set of commercial transactions are executed using one or more purchasing means that are registered by the patient with the cognitive medical decision support system.

17. The computer program product of claim 16, wherein the purchasing means comprises at least one of a credit card account identifier, a debit card identifier, an account identifier of an account associated with a provider of products, services, or activities, or a loyalty program identifier associated with a loyalty program of a provider of products, services, or activities.

18. The computer program product of claim 11, wherein information for the set of commercial transactions is obtained from at least one of a computing system associated with a financial institution with which the patient has a relationship or one or more computing systems associated with commercial establishments with which the commercial transaction is associated.

19. The computer program product of claim 11, wherein the computer readable program further causes the cognitive medical decision support system to evaluate the impact of the lifestyle behavior pattern at least by:
correlating, by the cognitive medical decision support system, the lifestyle behavior pattern with portions of an electronic medical record (EMR) for the patient based on categories of lifestyle behavior pattern information and categories of EMR information;
cognitively evaluating, by the cognitive medical decision support system, the correlations of categories of lifestyle behavior pattern information and categories of EMR information to identify changes in patient health, habits, or adherence to a prescribed treatment; and
identifying, by the cognitive medical decision support system, relevant patient information regarding changes since a last encounter between medical personnel and the patient based on the correlations, wherein the notification comprises an indication of the relevant patient information.

20. An apparatus comprising:
a processor; and
a memory coupled to the processor, wherein the memory comprises instructions which, when executed by the processor, cause the processor to implement a cognitive medical decision support system that operates to:
configure and train each of a plurality of lifestyle behavior pattern analyzers, by performing a machine learning process on a first set of commercial transaction data to learn weightings of lifestyle behavior factors present in the commercial transaction data relative to one another, to categorize a lifestyle behavior according to a predetermined set of lifestyle behavior pattern categories, and wherein each lifestyle data pattern analyzer is configured and trained by the machine learning process to identify patterns of data in commercial transactions indicative of lifestyle behavior patterns for a corresponding different category of commercial transaction data elements in commercial transaction data;

analyze, by artificial intelligence logic of the cognitive medical decision support system, a set of commercial transaction data structures defining a second set of commercial transactions executed by a patient to identify commercial transaction data elements corresponding to at least one of products or services purchased during each commercial transaction, or an activity, associated with the commercial transaction, engaged in by the patient;

determine, by the configured and trained plurality of lifestyle behavior pattern analyzers, a lifestyle behavior pattern of the patient based on detected patterns of commercial transaction data elements corresponding to at least one of products, services, or activities associated with the commercial transactions in the second set of commercial transactions;

evaluate, by the artificial intelligence logic of the cognitive medical decision support system, an impact of the lifestyle behavior pattern on at least one of a specific medical condition of the patient or a specific previously prescribed treatment of the patient, wherein the evaluation comprises processing the lifestyle behavior pattern of the patient, determined by the plurality of lifestyle behavior pattern analyzers, and patient electronic medical record data indicating at least one of the specific medical condition or specific previously prescribed medical treatment, through at least one cognitive analysis pipeline implementing the artificial intelligence logic of the cognitive medical decision support system; and output a notification indicating the impact of the lifestyle behavior pattern.

\* \* \* \* \*